United States Patent
Collura et al.

(10) Patent No.: US 9,706,939 B2
(45) Date of Patent: Jul. 18, 2017

(54) MULTI-CHANNEL, MULTI-VARIATE WHOLE-HEAD NORMALIZATION AND OPTIMIZATION SYSTEM USING LIVE Z-SCORES

(75) Inventors: Thomas F. Collura, Chagrin Falls, OH (US); William Mrklas, Streetsboro, OH (US); Theresia Collura, Chagrin Falls, OH (US)

(73) Assignee: BrainMaster Technologies, Inc., Bedford, OH (US)

( * ) Notice: Subject to any disclaimer, the term of this patent is extended or adjusted under 35 U.S.C. 154(b) by 1758 days.

(21) Appl. No.: 12/266,755

(22) Filed: Nov. 7, 2008

(65) Prior Publication Data

US 2009/0118636 A1    May 7, 2009

Related U.S. Application Data

(60) Provisional application No. 60/986,003, filed on Nov. 7, 2007.

(51) Int. Cl.
*A61B 5/0482* (2006.01)
*A61B 5/00* (2006.01)

(52) U.S. Cl.
CPC .......... *A61B 5/0482* (2013.01); *A61B 5/7264* (2013.01)

(58) Field of Classification Search
None
See application file for complete search history.

(56) References Cited

U.S. PATENT DOCUMENTS

2008/0091118 A1* 4/2008 Georgopoulos .............. 600/544
2009/0069707 A1* 3/2009 Sandford ...................... 600/545

OTHER PUBLICATIONS

Collura (Journal of Neurotherapy, 2008, vol. 12, pp. 99-110).*
Walker et al (Journal of Neurotherapy, 2007, vol. 11, pp. 25-44).*
Internet Archive Web page www.appliedneuroscience.com/QEEGNF.htm, (captured Apr. 8, 2006).*
Thatcher et al (Journal of Neurotherapy, 2003, vol. 7, pp. 87-121).*
Collura, T., 'The Atlantis Visual/Auditory/Tactile (V/A/T) Immersion System', AVS News, 2006, pp. 1-5).*
*EEG Biofeedback Training Using Live Z-Scores and Normative Database*, Collura, et al., Introduction to QEEG and Neurofeedback, Second Edition Elsvier, Inc., 2009; Chapter 5, pp. 103-141.
*EEG Biofeedback Case Studies Using Live Z-Score Training and a Normative Database*, Journal of Neurotherapy; Investigations in Neuromodulation, Neurofeedback and Applied Neuroscience, Collura, et al., vol. 14, Issue 1 (Feb. 2010).

* cited by examiner

*Primary Examiner* — Karen Canella
(74) *Attorney, Agent, or Firm* — Walter | Haverfield LLP; D. Peter Hochberg; Sean F. Mellino

(57) ABSTRACT

A method of whole-brain EEG neurofeedback training of a trainee using live Z-scores from 4 channels of EEG signals to acquire 248 Z-scores from 6 simultaneous interconnectivity paths. The feedback system is endowed with the ability to establish training targets and to use derived metrics to produce feedback of an auditory, visual, vibrotactile, or other sensory or direct nature. The feedback signals are determined by a multivariate analysis that takes into consideration how measured variables compare with predefined criteria, thus producing a statistical correlation in real-time, in conjunction with a reference or normative database, rule-set, algorithm, discriminate function, or classification system.

14 Claims, 11 Drawing Sheets

MULTI-CHANNEL, MULTI-VARIATE WHOLE-HEAD NORMALIZATION AND OPTIMIZATION SYSTEM USING LIVE Z-SCORES

RELATED APPLICATIONS

This application is a conversion of U.S. provisional application 60/986,003, filed Nov. 7, 2007.

STATEMENT CONCERNING GOVERNMENT SPONSORSHIP

No part of this application was sponsored in whole or in part by the U.S. government.

FIELD OF THE INVENTION

The disclosure of this application is in the general field of neuroscience and neurological biofeedback training and conditioning.

BACKGROUND OF THE INVENTION

Drawing from a consideration of the cellular basis of EEG biofeedback and an understanding of neuronal functions, it is possible to view EEG and EEG operant training as a form of normalization training that emphasizes brain self-regulation, in an objective and scientifically driven approach towards integrated brain function.

It is instructive to begin at a basic level, which is that of individual cortical brain cells. FIG. 1 is an interior view of a typical neuronal assembly (not to scale), and shows a figurative view of layers I-VI of a cortical neuronal assembly. The cells marked "P" are the pyramidal cells, which are the primary processing elements in the neocortex. This view is the same in various areas of the cortex, and is thus applicable whether the cortex is sensory, perceptual, executing motor control, planning, or memory. In all cases, the pyramidal cells are mediated by an extensive network of interneurons (marked "H", "F", "B", "N", "M", and "S") which communicate between and among themselves, as well as with the pyramidal cells. The majority of interneurons are inhibitory. Without this inhibitory influence, incoming upstream ("afferent") neuronal impulses would produce an overabundance of action potentials in the downstream ("efferent") neurons, ultimately leading to a chaotic excess of meaningless activity.

The inhibitory interneurons have significant influence, and condition the downstream neurons so that action potentials can only be produced as a result of persistent, accumulated afferent signals. By modulating the extent and magnitude of the inhibitory interneuronal activity, the brain can tone down activity, so that the cortex generally has a manageable level of activity, providing useful information processing and control. Another manifestation of essential inhibition is "lateral inhibition" in which adjacent neurons have a tendency to inhibit each other's activity. This phenomenon is essential to retaining the acuity of sensory processes, as it prevents the spreading of incoming activity, and ensures that a fine level of detail can be preserved as signals are conducted from the peripheral sensory organs, through sensory pathways, into and through the sensory areas of the cortex.

The EEG sees the millivolt-level postsynaptic activity of pyramidal cells in the form of microvolt-level surface potentials that are conducted from the cortex to the scalp via volume conduction. It is when pyramidal cells polarize synchronously that they produce a measurable potential. Generally, the action of these cells is not highly synchronized, so that their external potentials cancel out at the scalp. However, when even a small number of cells polarize in a synchronous fashion, they produce a measurable surface potential. This phenomenon is so extreme that less than 5% of the pyramidal cells are capable, when synchronized, to control over 95% of the overall EEG. EEG signals are further spread or "smeared" as they reach the cortex, so that a given surface sensor is able to detect activity not only from the cortex directly below, but also from areas distant from the sensor, as shown in FIG. 2.

FIG. 2 shows the effect of EEG "blurring" on the distribution of surface potential produced by a given cortical generator, where the signal is maximal near Fz, yet is detectable in varying amounts across the entire scalp. As a rule of thumb, approximately 50% of the energy detected by a 10-20 site is produced by the cortex lying below the sensor, while the other 50% is produced by adjacent, as well as more distant, sites.

FIG. 3 schematically shows a figurative view of the combined activity of multiple neuronal assemblies, their interconnections, and the production of BEG. This simplified representation shows that there are multiple neuronal assemblies, all interconnected in various ways, and all producing their contribution to the overall BEG signal. Whereas the synchronous activity of a given neuronal assembly can produce its portion of the EEG, the connections among neuronal assemblies are responsible for the connectivity measurements (coherence, phase, etc) that can be measured between sites.

The Role of Inhibition in Neuronal Dynamics

The brain is a hyper-connected system. Each of the billions of cortical neurons has thousands of connections to other neurons, and these include both short-length and long-length connections. It is possible to connect from a typical cortical neuron to any other cortical neuron in just a few "hops." The reason that the brain does not descend into chaos it that the vast preponderance of interneuronal connections are inhibitory, thus holding rampant neuronal firing at bay. It is the inhibitory influences that carve out the fine structure of connectivity. EEG biofeedback works by allowing the brain to adjust inhibitory connections, to potentiate or to remove connections, and to enable or disable particular locations. It is inhibition that allows structure to emerge in the system. Interneurons inhibit the release of GABA on the part of the pyramidal cells. Inhibitory connections suppress irrelevant communication while preserving relevant communication. Generally, elevated coherence indicates that the system is not inhibiting irrelevant signals sufficiently to sculpt the cortical responses.

The primary mechanism of neuronal control is inhibition. Whereas most neurons are intrinsically excitable, and if left isolated, will produce action potentials, the majority of interconnections are inhibitory, thus holding neuronal firing at bay. It is when inhibition is reduced that the neuronal assembly has an increased ability to respond to afferent signals, and to participate in rhythmic activity. Thus, the regulation of brain rhythms has, at its core, the control of inhibitory processes, such that the relaxation of inhibition facilitates the production of observable brain rhythms.

This rhythmic activity falls into two broad categories, which are thalamocortical reverberation, and corticortical communication. Thalamocortical reverberation consists of repetitive activity mediated by a cyclic pattern of signals coming up from the thalamus to the cortex, and from the cortex down to the thalamus. Typical delays for thalamocortical signals are between 40 and 80 milliseconds per transmission. Thus, a two-way transfer, comprising one cycle, will take between 80 and 160 milliseconds. As a result, thalamocortical oscillations are typically observed with frequencies between 8 cycles per second and 15 cycles per second. Oscillations in the range of 8 to 12 cycles per second are designated as alpha waves, and are evident throughout the brain, but are most pronounced in the occipital cortex, particularly when the eyes are closed. Oscillations in the range of 12 to 15 cycles per second are also observed generally, but are most pronounced over the motor strip during periods of stillness, and these are designated as the sensorimotor rhythm, or SMR.

Overall, the brain is continually modulating and tuning the inhibitory processes within and between neuronal assemblies, and this is a primary method for the control of brain processes in general. The innate control of rhythms, comprising a cycle of concentration and relaxation, is essential for the performance of tasks in an effective and efficient manner. There is a general inhibitory tone that is evident for an individual in the various cortical areas, which contributes to the overall functional orientation. For example, if one presents with an underactive frontal cortex, we generally associate this with a lack of control, inability to plan, and a propensity for impulsive behavior. Superimposed on this general tone is the ability to modulate cortical excitability from moment-to-moment. This ability to modulate in a manner that is flexible and appropriate underlies the ability to be in a suitable state at a suitable time, thus enabling the individual to behave in an adaptive and efficient manner.

The graph in FIG. 4 illustrates the range of concentration and relaxation along a continuum. At any given instant, any neuronal assembly is predominantly in some location along this continuum.

There is a tendency to view neurofeedback in terms of a model of making "big things small" or making "small things big." That is, the view is that something in the activity of the brain is present in an amount that is too much, or too little, and needs to be "fixed." According to the present view, however, we look at the time-behavior of neuronal activity, and understand that the traditional "amplitude" measurements are more of a reflection of "how often" or "how rare" a given brain state is, within the context of overall neuronal time course. Neurofeedback is thus not so much an issue of pushing rhythms up or down, but more one of teaching the brain to find alternative activation states, and to integrate them into its modes of functioning.

Normative assessment is an attempt to understand an individual's brain rhythms in terms of quantity and connectivity, in relation to a population that is regarded as normal or average. It is thus possible to assess the fine-tuning of the brain as a complex system, and to understand how well, or how poorly, a given brain corresponds to a "normal" brain, in terms of these activation and connectivity patterns.

It is possible to see deviations from normal that are not in themselves harmful or detrimental. Some of these fall under the category of "peak performance" attributes. Others can be viewed as individual differences that are not necessarily related to any clinical or personal complaint.

"Healthy" deviations include non-harmful "excesses" such as elevated alpha waves or SMR waves, in certain cases. In other cases, elevated alpha can reflect a coping mechanism in cases of chronic anxiety. Similarly, reduced alpha may be simply reflect an individual style oriented toward more activation than is typical. However, in cases of chronic pain, reduced alpha may reflect a tendency toward heightened neural tone, indicating an inability to relax, and a state of chronic high arousal.

Normalization of the EEG provides the opportunity for the individual to find a more stable neuronal configuration. It does not in itself provide a "cure" for a disorder. Rather, it allows the brain to find an alternative set of stable dynamics, which the individual can now utilize in the course of thought and action.

When normalization is appropriate and complete, things that were not targeted can be seen to normalize. However, when normalization is partial, it is possible for the brain to find other avenues to express its dysregulation. This leads to the concept of "neuronal hydraulics" which states that if we push on the system without holding sufficient variables constrained, the system may find other outlets, and other dysregulation may express themselves. This is a well-known and documented phenomenon in the pursuit of connectivity training.

In neurofeedback training, we provide the brain with the opportunity for change, and the brain works out the internal details using its own mechanisms. We may be presented with a brain that has various stress orientations, and provide the information that helps is to find a more relaxed and appropriate set of states. The brain spontaneously seeks its own stability and homeostasis, subject to the internal and external information with which it can work. Whereas a given individual may have cortical locations that are under-aroused, over-aroused, under-connected, or over-connected, the brain copes with its condition by trying to do the best job of regulating states and behavior, subject to the constraints of neuronal dynamics and change. The things we view as symptoms are emergent properties of a system that is in what it regards as an optimal state, given its past history and physical resources. Neurofeedback provides the ability to change by providing additional information, thus altering the experiential framework within which the brain can seek stable states of operation.

Z-Score Neurofeedback

One approach to providing the brain with the information it needs to self-regulate is called Z-Score neurofeedback. Z-Score neurofeedback uses the normative data from a specific data base, to provide real time feedback of a variety of comparisons of current brain amplitudes at various frequencies, along with coherence and phase computations among multiple sites with normative values. So any variable that differs significantly from the normative data base will be highlighted instantaneously. Z-scores are deviation scores, valued in terms of standard deviations, so that a Z-score of one indicates that this variable is 1 standard deviation different from the normative value. The actual feedback can be an auditory tone or a visual animation, and may represent a single Z-score value, such as Beta amplitude at Cz, or may be a composite of many Z scores representing multiple sites, amplitudes, coherences, and phase relationships.

Live Z-score training (LZT) and methods use live Z-scores to view EEG parameters for simple training. Live Z-score training (LZT) with 1, 2, and 4 channels is known. Initial implementation gave access to any of the possible Z-scores, through a general, flexible mechanism, called the "Event Wizard." This was used to construct basic protocols using single Z-scores, Z-score range training, and combined Z-score training such as "all coherences normal." From there, we moved to "range training", in which one or more Z-scores can be trained within a range.

Simple LZT training works well. However, simple single-component training has serious limitations. The additional power in the design of complex protocols would be of great value. For example, training a single parameter from a single component band is not optimal. Training all component bands in a given metric ensures a more comprehensive training for purposes of local neuronal activation or relaxation. Similarly, when more than 1 channel of EEG is available, it is beneficial to incorporate all channels into the training, to provide greater coverage and specificity, and to address connectivity.

The LZT DLL that underlies the approach in this application provides Z-scores for 6 important metrics: absolute power, relative power, and power ratios for each channel, and coherence, phase, and asymmetry for each pair. Thus, 1 channel of EEG provides 26 Z-scores, 2 channels provide 76 Z-scores, and 4 channels provide 248 Z-scores. The use of 4 channels in accordance with the present disclosure and invention is a significant advancement, as it provides data on 6 simultaneous interconnectivity paths, not just 1, and thus provides a gateway to whole-brain training.

Regardless of the number of channels used or the Z-score training strategy, feedback has generally consisted of animations, DVD's, games, sounds, music, and other typical displays. The trainees are not necessarily aware that they are using an entirely new form of training. They are only aware of the brain states into which they are being guided.

The combination of proper QEEG methods, along with a well-planned neurofeedback program of protocols based upon live Z-scores, can provide an accelerated and highly targetable regimen.

It is important to train coherence within a proper range, as there are dangers inherent in training any particular coherence in one direction. Z-scores provide an important relief of this concern, by ensuring that coherence targets are appropriate for the individual. However, even training a single coherence toward normal may not be optimal, given how the brain may respond to an excessively focused training protocol. In one instance, although individual connectivities were normalized in the initial treatment, the untrained connectivities exhibited severe instability, and their compensatory changes led to abreactions visible both in the EEG and clinically. It is generally not possible to normalize connectivity of the brain using only a single pair of channels. To the contrary, it is possible to cause abreactions of various types, whenever attempts are made to alter the coherence of one particular band in one particular pathway.

In an example of the importance of whole-brain connectivity training, a single coherence between two sites is targeted for neurofeedback training, and is effectively altered. However, as that coherence normalized, other coherences in the brain became abnormal. Even without the trained connection moving toward hypocoherence, the rest of the brain had maladapted to the training.

The inquiry is how and why the brain would respond in this way to the information being fed back. The brain, like any dynamical system, will seek the minimum-energy pathway to satisfy external and internal constraints. Indeed, one may posit a model of "brain hydraulics" in which various constraints are at work. These may variously be regarded as tendencies or pressures, which give rise to the flow of information and control, thus reflecting the cybernetic activity of the brain.

There has been proposed a predator-prey model that describes the mediation between short-range connections and long-range connections in the brain. According to this model, each neuron has a limited resource of inputs and outputs, which it must allocate between the various connections available, including both short-range and long-range connections. As the brain trades off between these connections, changes in coherence and phase metrics will reflect this dynamic reorganization.

SUMMARY OF THE INVENTION

In biofeedback systems, it is necessary to produce a signal that represents some aspect of the trainee's physiology, and to feed this back in a form suitable for learning. The established approach for achieving this goal is to record a physiological signal such as temperature, muscle, or brain activity, and to produce a suitable feedback system to train the individual towards a stated goal. Thus, training has traditionally been oriented towards raising or lowering particular values, and the use of thresholds to determine limits of feedback. Even with more complex systems, feedback is based upon a simple combination of signal criteria, and the attempt to train the individual to essentially steer the physiological signals in a direction consistent with the therapeutic goals.

In this invention, the feedback signals are determined by a multivariate analysis that takes into consideration how measured variables compare with predefined criteria, thus producing a statistical correlation in real-time, in conjunction with a reference or normative database, rule-set, algorithm, discriminant function, or classification system.

In this invention, the feedback system is endowed with the ability to establish training targets in terms of the aforementioned criteria, and to use derived metrics to produce feedback of an auditory, visual, vibrotactile, or other sensory or direct nature.

The system computes derived metrics and scores based upon physiological parameters which may include the electroencephalogram (EEG), hemoencephalogram (REG), electromyogram (EMG), electrocardiogram (EKG), heart rate (HR), heart-rate variability (HRV), galvanic skin response (GSR), or other physiological variables.

Rather than referencing feedback to a particular physiological quantity, this method references the feedback to a state which may be defined in multiple dimensions. The dimensionality of the feedback variable is no longer a simple measure such as temperature, energy, concentration, relaxation, or other one-dimensional aspect. Operant condition can then proceed based upon a complex inner model of state-variability, rather than a single physiological variable.

This invention produces and uses standardized and referenced information useful in real-time for guiding physiological states via learning mechanisms including operant and concurrent learning. Computed values may be any of a range of possible metrics including peak or absolute frequency, and connectivity metrics including coherence, phase, asymmetry or synchrony.

With this invention, it becomes possible to compose complex protocols based upon criteria defined in terms of multiple variable characteristics and statistics, that guide the individual toward complex self-regulation tasks.

DESCRIPTION OF THE DRAWINGS

FIG. 5 is an example of a typical 4-channel Z-score display.

Figure 1:
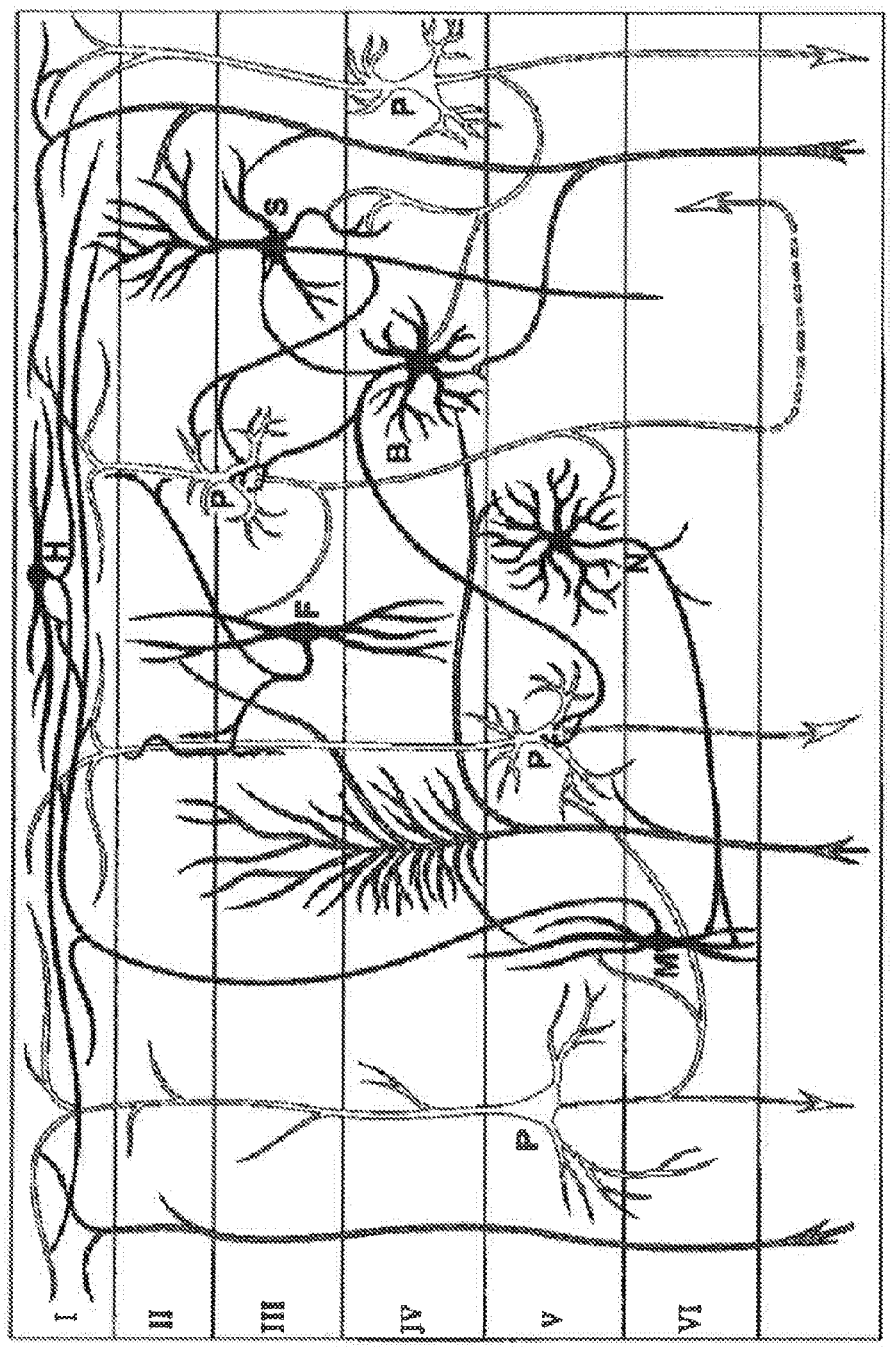
FIG. 1 is an interior view of a typical neuronal assembly.
Figure 2:
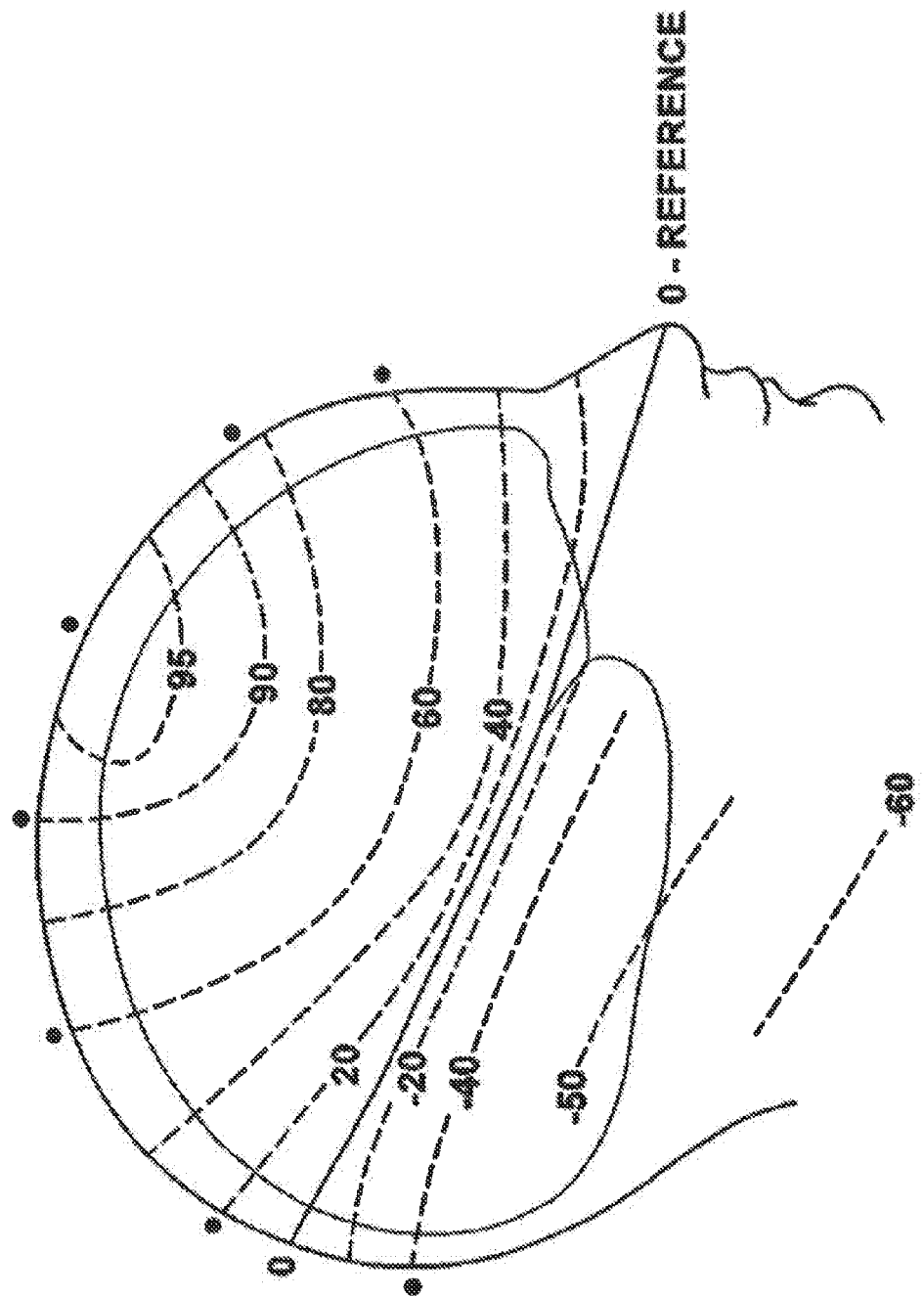
FIG. 2 shows the effect of EEG "blurring" on the distribution of surface potential produced by a given cortical generator.
Figure 3:
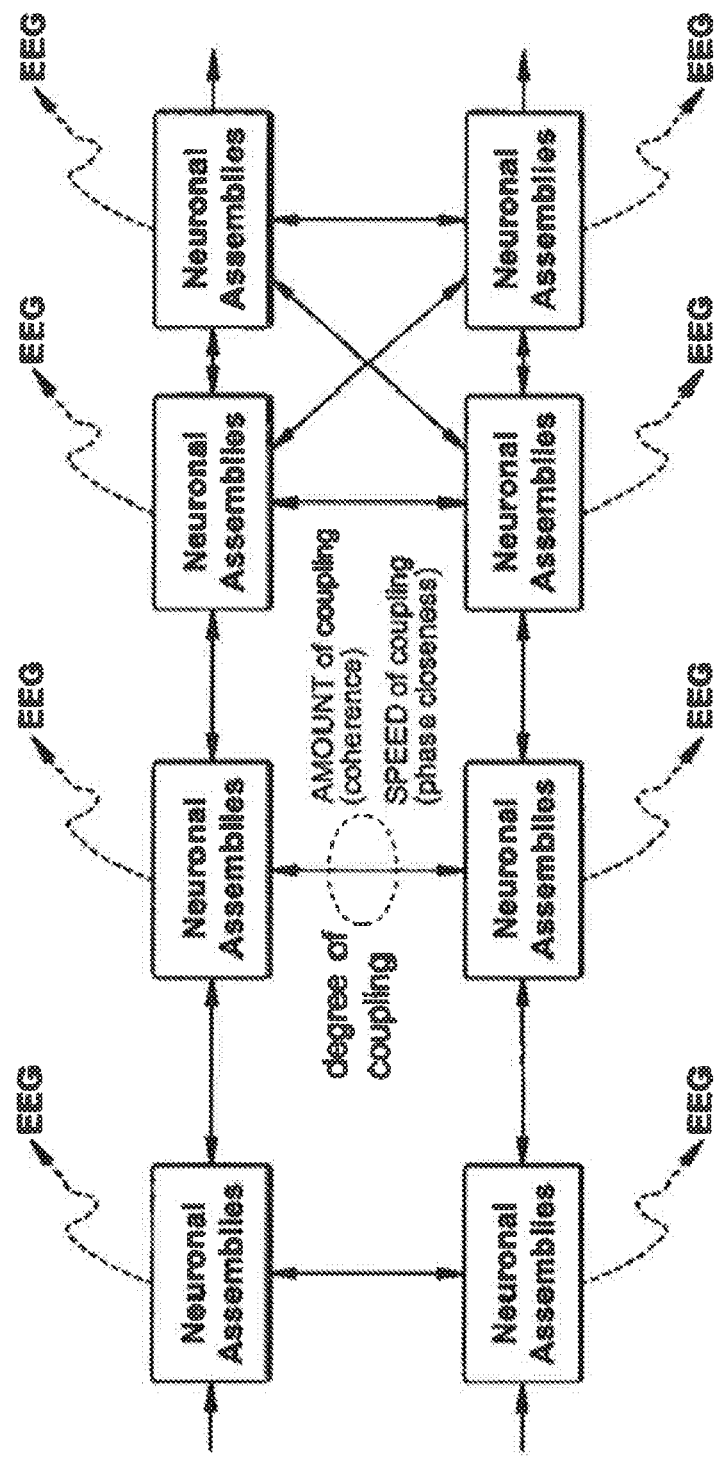
FIG. 3 is a figurative view of the combined activity of multiple neuronal assemblies, their interconnections, and the production of EEG.
Figure 4:
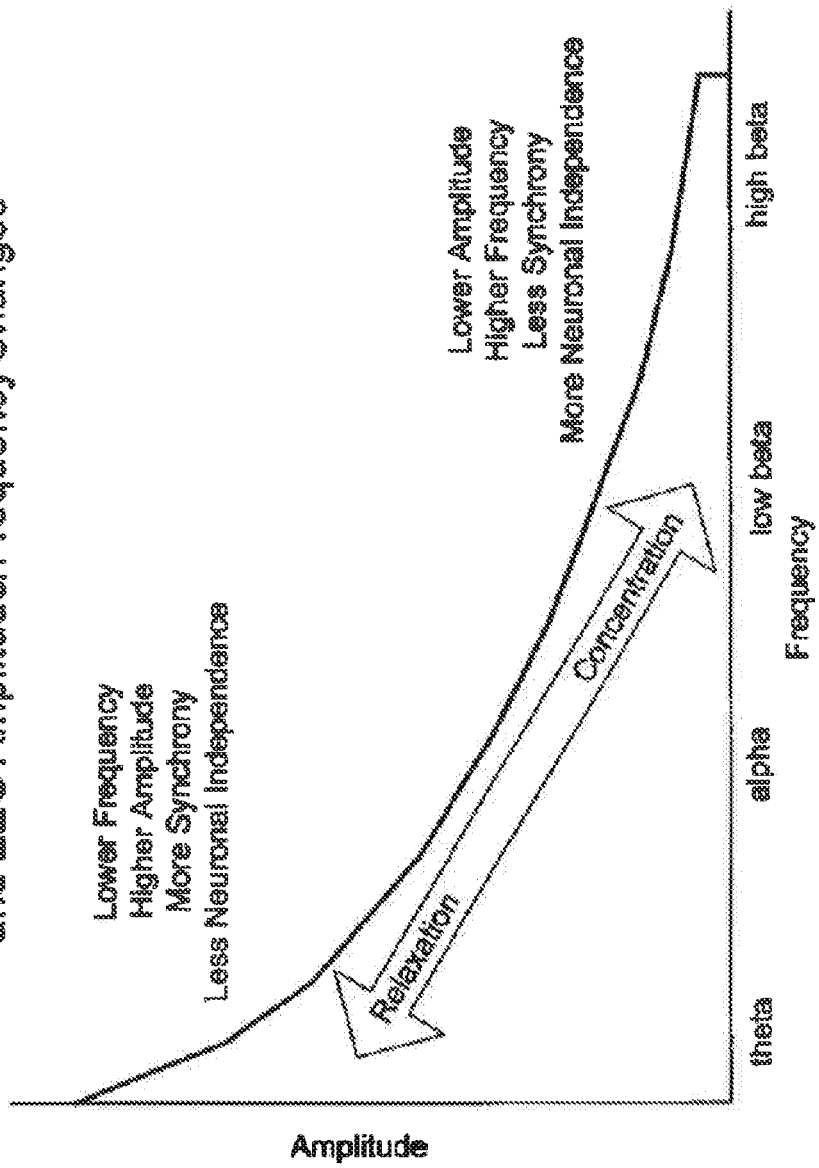
FIG. 4 illustrates the range of concentration and relaxation along a continuum.

DETAILED DESCRIPTION OF PREFERRED AND ALTERNATE EMBODIMENTS OF THE DISCLOSURE AND INVENTIONS

From live Z-score training (LZT) and viewing of EEG parameters for simple training, the present disclosure is of a comprehensive multichannel whole-head approach with an underlying rationale and a growing set of advanced protocols.

Specifically, the LZT DLL that underlies the approach in this application provides Z-scores for 6 important metrics: absolute power, relative power, and power ratios for each channel, and coherence, phase, and asymmetry for each pair. Thus, 1 channel of EEG provides 26 Z-scores, 2 channels provide 76 Z-scores, and 4 channels provide 248 Z-scores. The use of 4 channels in accordance with the present disclosure and invention is a significant advancement, as it provides data on 6 simultaneous interconnectivity paths, not just 1, and thus provides a gateway to whole-brain training.

A brain model is disclosed in which the response to neurofeedback training is in the form of a variety of adjustments which, through learning, tend to have a lasting nature. In the case of amplitude-based training, changes take the form of changes in cortical relaxation produced by alternating the strength of individual inhibitory connections, thus modulating cortical excitability, and thalamocortical cycling tendencies, for the affected conical locations and pathways. Other metrics are more related to connectivity, such as coherence and phase, and the changes they introduce are different in nature. They include the structured rearrangement of the neuronal connection strengths, in order to comply with the training conditions.

When the conditions are limited, then the brain's response may be similarly limited.

This does not mean that the training effect is limited to the training area. Quite the contrary. Both beneficial as well as adverse responses may occur. Thalamic pathways, as well as various cortical interconnections are involved. The use of Z-scores has made evident patterns and time-dependent shifts in the full complement of Z-scores, with phase as a primary adjuster, then wave of re-organization.

A single Z score is just a target re-implemented. Especially in cases of connectivity metrics, it provides a valuable aid to determining and using target values. It can also be useful when used in a ranged fashion (high and low thresholds), to train within a range. However, targeting a single connectivity metric, although it may be trained within a normal range, can cause other reactions in the brain, which are not necessarily beneficial.

It is believed to be important to use multiple channels with Z-scores, and to use the information effectively. A minimum of 2 channels are needed in order to see the pathway between them, and compute coherence, phase, and asymmetry metrics. But when 4 channels are used, the number of connections is 6, which is significantly more information. In accordance with the present disclosure and invention, multiple connectivity training is a significant capability and strength of live Z-Score training.

Four channels are sufficient to ensure coverage of the basic interconnections in a given training paradigm, including channels for measuring left intrahemispheric function indicative a language ability; right intrahemispheric function indicative of spatial ability; frontal intrahemispheric function indicative of attention and planning abilities, and posterior intrahemispheric function indicative of sensation and perception abilities.

Examples of typical arrangements include F3-F4-P3-P4 and C3-C4-Fz-Pz. With a MINI-Q, it is possible to define predefined layouts of 4 channels that emphasize different brain connections and activities. Furthermore, these predefined "quads" can be used for assessment as well as training, providing a unified approach to whole-brain work.

In the case of F3-F4-P3-P4, for example, we have not only 4 important brain sites, but also 6 important connection pathways. This 4-channel montage allows us to monitor both the left and right frontal areas, and the left and right posterior areas. It also provides information relating to left intra-hemispheric function (language), right intra-hemispheric function (spatial, etc), frontal inter-hemispheric function (attention, planning), and posterior inter-hemispheric function (sensation, perception). This is a very simple, yet comprehensive way to gain access to EEG information for training purposes.

As used herein, the following terms having the ascribed meanings.

"Z score": A deviation of real-time EEG values (phase, amplitude, absolute power, relative power, power ratios) from normative values. A Z-score is a measure of how much a measured value deviates from normal. In the subject embodiment, the measures include absolute power (size of the signal), relative power (size of the signal relative to another signal), power ratios (ratios of different component bands), coherence (measure of phase stability over time), phase (measure of phase separation), and asymmetry (ratio of power to power in another channel).

"Live Z-scores" means Z-scores which are acquired from a trainee during neurofeedback or biofeedback to the trainee.

"Protocol": A set of rules and instructions that define how the biofeedback system will respond to specific signal attributes. Protocol design includes identification of the values being measured, the values they are being compared to, and rules such as to produce feedback when a threshold is exceeded, or is within a particular range. In existing systems, the values measured are physiological variables such as blood pressure, skin temperature, or EEG alpha waves. In the present disclosure and invention, the measures are statistical measures that reflect how the subject's physiology compares with certain reference criteria.

"Channels": A signal defined over time, such as an EKG or EEG signal. A biofeedback system may have one channel, e.g. 1 temperature, or it may have 2 channels, such as temperature and skin resistance, or it may have many channels, such as 4 channels of EEG.

"Normalization": A process by which a system finds its normal operating conditions and parameters. Biofeedback teaches an organism to find its own normal physiology by making adaptive changes, without introducing external agents. It is a form of learning, therefore, that produces desired changes via operant conditioning and related mechanisms.

"Interconnectivity paths": "Neuorpathway connections between and among different areas of the brain. These include axonal tracts, cortical fasciculi, and other neuropathways that are used to send information to and from the brain, and between brain areas.

"Whole brain (or whole head) training": The use of techniques that use data regarding the entire brain or head, in establishing EEG biofeedback protocols. Whole brain training requires the acquisition of at least 4 channels of EEG, and the development of protocols that adequately reflect the activity of the whole brain in the biofeedback system.

"Coherence": A measure of the relationship between two signals, or two parts of the brain, if the signals are EEG. It reflects the stability of the phase relationship between the signals. It is thus a measure of the amount of information sharing between the brain areas, hence reflects functional communication in the brain.

"Phase": A measure of the separation of two signals in time. In the case of EEG waves, phase reflects the speed of information sharing or transfer between two brain areas. It is thus relevant to the efficiency of information processing as the brain works as a system.

"Multivariate Proportional (MVP)": A measure of the proportion of variables in a multivariable space that meet a criterion condition. Thus, the proportion becomes a measure of proportionality, i.e., how well the system fits into that space. In certain cases, MVP variables can be interpreted as how normal the brain is, and can take typical values of from 0 percent to 100 percent. MVP variables can also reflect other attributes of the system. In all cases, they are designed to reflect what proportion of the variables meet some condition.

Figure 5:
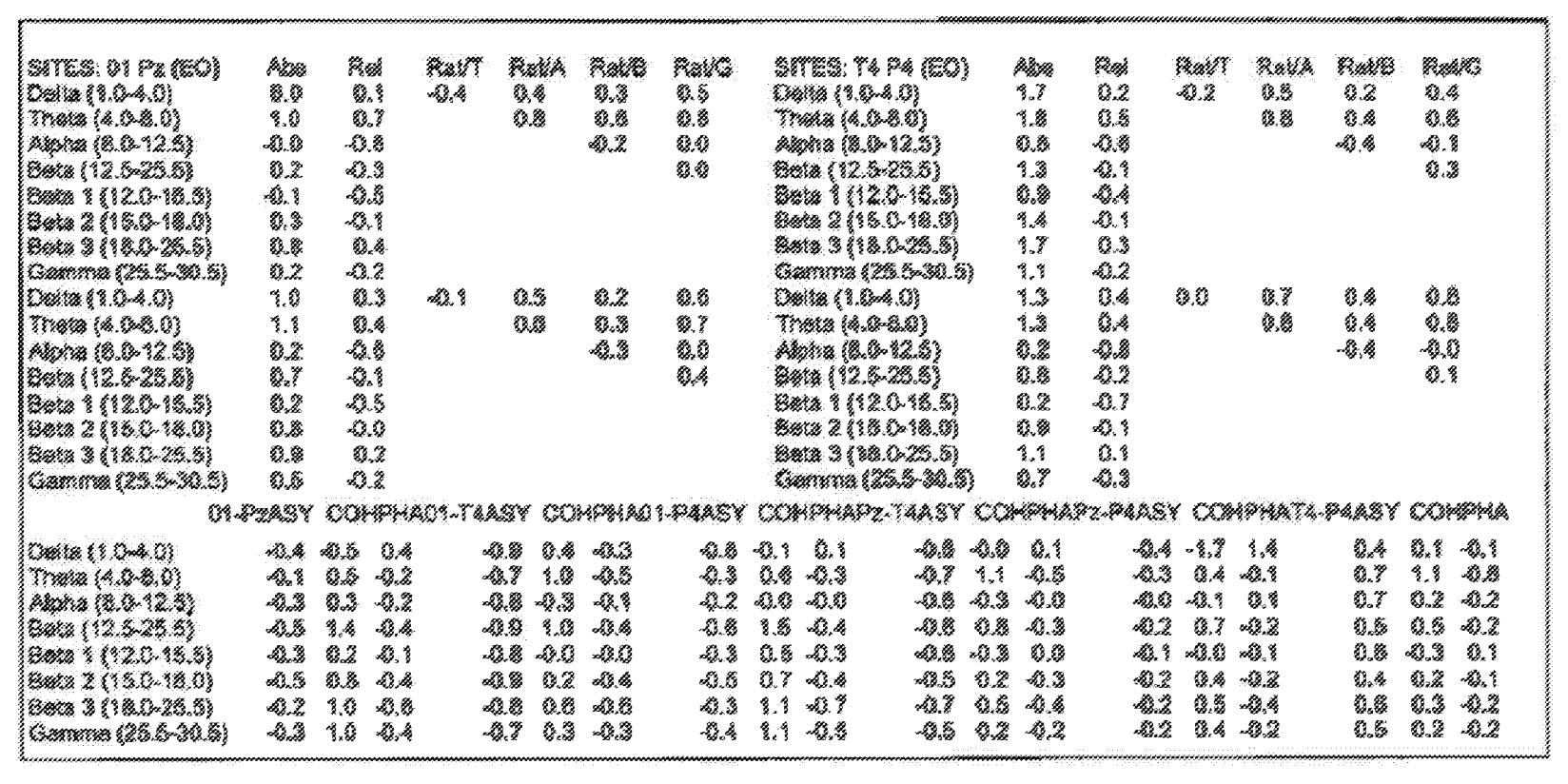

FIG. 5 shows an example of a typical 4-channel Z-score display from the system, providing 248 Z scores. The sensors for FIG. 5 are located at O01, Pz, T4, and P4. Our software automatically compiles, displays, and computes complex training statistics based on all of the available scores. There are a total of 248 Z-scores available. The indicated Z-scores may be dynamically color-coded in a manner that makes it easy to spot deviations. The power-based Z-scores are clustered at the top of the display, and the connectivity metrics are shown at the bottom of the display.

It is not possible to understand the dynamics of brain response by watching a single Z-Score, or even a small number of Z-Scores. It is necessary to simultaneously monitor the full range of variables in a suitable number of sites, in order to observe the dynamical brain processes. To relieve these concerns, it is necessary to implement a comprehensive brain training method. The disclosed methods simultaneously address issues of activation and relaxation, connectivity in the form of communication and control, and relative activation.

A series of advanced multichannel, multivariate training methods are disclosed, which are alternatively collectively described as "Multivariate Proportional," or "MVP". The MVP training methods include and utilize multivariate proportional algorithms that automatically incorporate all of the available Z-scores for all channels acquired, and compute continuous output values in the form of multivariate proportional variables which represent a percentage measure of a proportionality of the Z-scores which are within predetermined ranges, and are in essence figures of merit for the Z-score set. The MVP score is thus truly a complex measure of "how normal" the EEG is, when accounting for all available information.

The system and method have established that multivariable training with LZT is not too complex for the trainee to comprehend. To the contrary, during the training, in an exemplary embodiment the subject is simply watching a DVD or animation, or playing a game, or listening to music or sounds. The complex protocol calculations still control all feedback as if they were just another training variable. The trainee experience can be whatever is conventional or familiar, relative to the "signaling" method. The brain readily seizes on information that relates to a well-targeted state, regardless of the metrics underlying the state. That fact that we can ride a bicycle demonstrates that we can readily integrate millions of bits of information into a cohesive whole, combined with the mind and body responses, and that it can become effortless. The more comprehensive the information, the more likely the brain is to understand and interpret it. And this is a brain process, not a conscious mental process.

This is not unlike the difference between simple muscle fitness training, versus a more comprehensive activity like dance or athletics. When applied in a comprehensive whole-head training approach, live Z-scores transform neurofeedback into an entirely different kind of experience for the brain's self-regulatory mechanisms. Nonetheless, the trainee continue to watch movies, play simple games, listen to music, as before, and by allowing the training to occur, lets their brain learn a new and profound new set of activations and connections.

In a preferred practice of the disclosure and invention, a comprehensive MVP method is used which incorporates all available Z-scores into a single metric. The system and method preferably includes selective training functions, such as training only a specific metric (absolute power, relative power, etc), or training a certain class of metrics ("all connectivity metrics"), and the ability to use different upper and lower limits. In the case of a trainee who has excessive amplitudes overall, reaching the level of 2-3 standard deviations in the dynamic scores, limits are required. When a window of + or –3 standard deviations was used for training, the trainee's EEG quickly changed to a very low amplitude EEG, and overshot the goal of zero. Therefore, we provided the ability to provide different limits, and the trainee was trained using limits of +3 and –1 standard deviations. This allows effective feedback, while not rewarding the trainee for going too low.

Using a comprehensive approach, it is also possible to address the issue of normalization training versus peak-performance or mental-fitness training. Based upon experience with various peak-performers, there have been identified certain combinations of features that are unique to them. Subjective reporting data on individuals who undergo Z-score training, and who exhibit one or more of these characteristics indicates that certain characteristics are generally identifiable as "good" and which reflect optimal functioning for that individual (but not necessarily all individuals). Other characteristics may be observed, that are concordant with "complaints," which might include issues with attention or mood.

Figure 6:
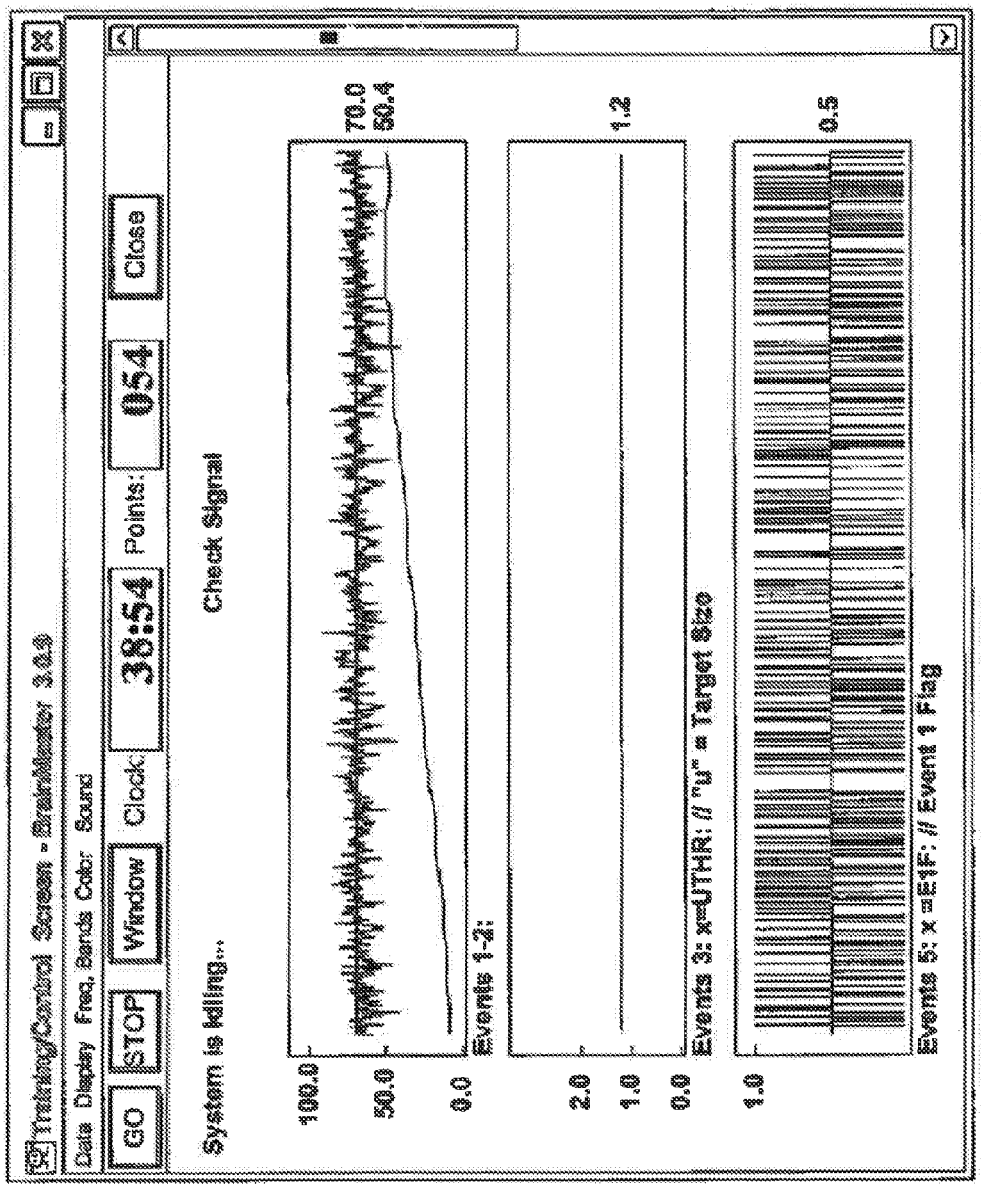
FIG. 6 is an example of a typical indicator screen used with a Multivariate Proportional (MVP training protocol.

FIG. 6 shows an example of a typical indicator screen used with a Multivariate Proportional (MVP) training protocol. The white markings on the top chart show the MVP training parameter. The green markings on the top chart show the MVP target percentage threshold, in this case 70%. The red makings on the top chart show the cumulative percent time above threshold, in this case 50.4%. The middle chart shows the size of the target in standard deviations, in this case 1.2. The bottom chart on FIG. 6 shows an event flag indicating the times when the MVP parameter is above threshold.

Despite the complexity of the underlying computations, the display and its interpretation are relatively simple. The system derives a metric which reflects a comprehensive analysis of all of the Z-scores, or a subset thereof. The metric becomes the training variable, thus replacing the conventional amplitude or connectivity-based metric, and is significantly more comprehensive than a single Z-score.

The interpretation of the overall success rate is identical to that in any operant conditioning paradigm, and reflects the aggregate reward being experienced by the user. The variables that can be adjusted to control feedback are the target size and the performance score required for the derived metric. In the example shown, the required score is 70.0 percent, and the trainee is achieving this goal 50.4 percent of the time, on average.

One benefit of MVP-based protocols is that they can be biased for peak performance. For example, among the attributes that may be selected for enhancement are global alpha coherence, resting motor strip SMR, reduced low-frequency coherence, or other variables. These protocols thus combine the concept of brain normalization with that of brain optimization.

Figure 7:
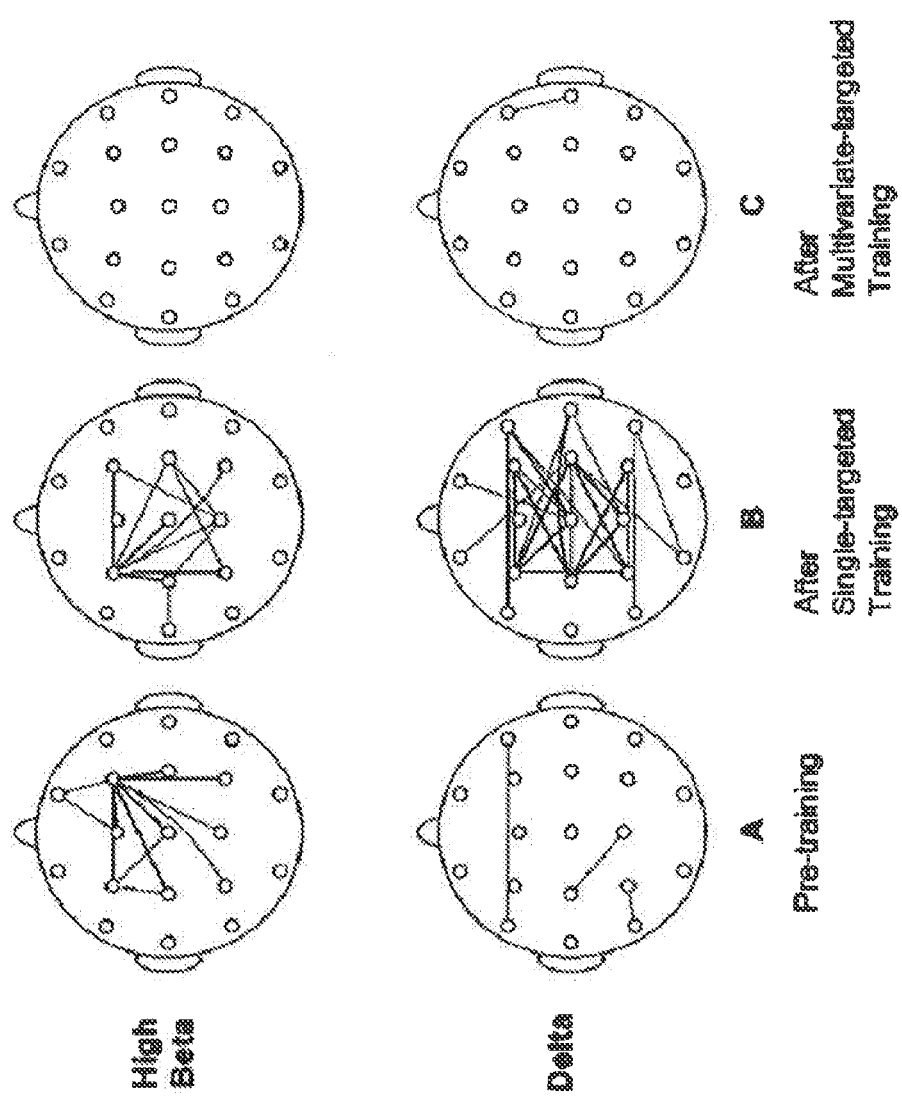
FIG. 7 illustrates three NeuroGuide QEEG coherence maps from a full 19-channel assessment.

In the example shown in FIG. 7, three NeuroGuide QEEG coherence maps are obtained from a full 19-channel EEG assessment. The NeuroGuide coherence maps in FIG. 7 show High Beta and Delta coherences before training, after a single-targeted training regimen, and after MVP training.

The first map in FIG. 7 shows the trainee at an early stage in this training experience. Considerable coherence abnormalities (hypocoherences) are evident. The second map shows the effects of conventional targeted coherence training, using the following plan:

1. Increase coherence of beta at F4/C4 to decrease seizures. (5 sessions)
2. Increase coherence of delta at P3/T5 to decrease seizures. (5 sessions)
3. Increase coherence of delta at F7/F8 to decrease seizures. (5 sessions)
4. Increase coherence of beta at C4/F8 to decrease seizures. (5 sessions)

The effects of the training are evident. The targeted coherences have indeed moved toward normalization. However, many coherences that were not targeted have changed, and not for the better. Furthermore, delta coherences have become significantly worse. This demonstrates the potential hazards of targeting single coherence measures along single connectivity paths. The third (right) map shows the result after several sessions of multivariate targeted coherence training. It is evident that the multichannel, multivariate approach is indeed capable of targeting and normalizing a comprehensive set of coherences, leading to whole-brain normalization.

These advanced multivariate training methods are implemented in software, and are applied "on top" of the basic live Z-score software that is built into the ANI DLL. This software is itself written in the form of a library, which can become available to other system developers, who wish to incorporate this new form of training.

Figure 8:
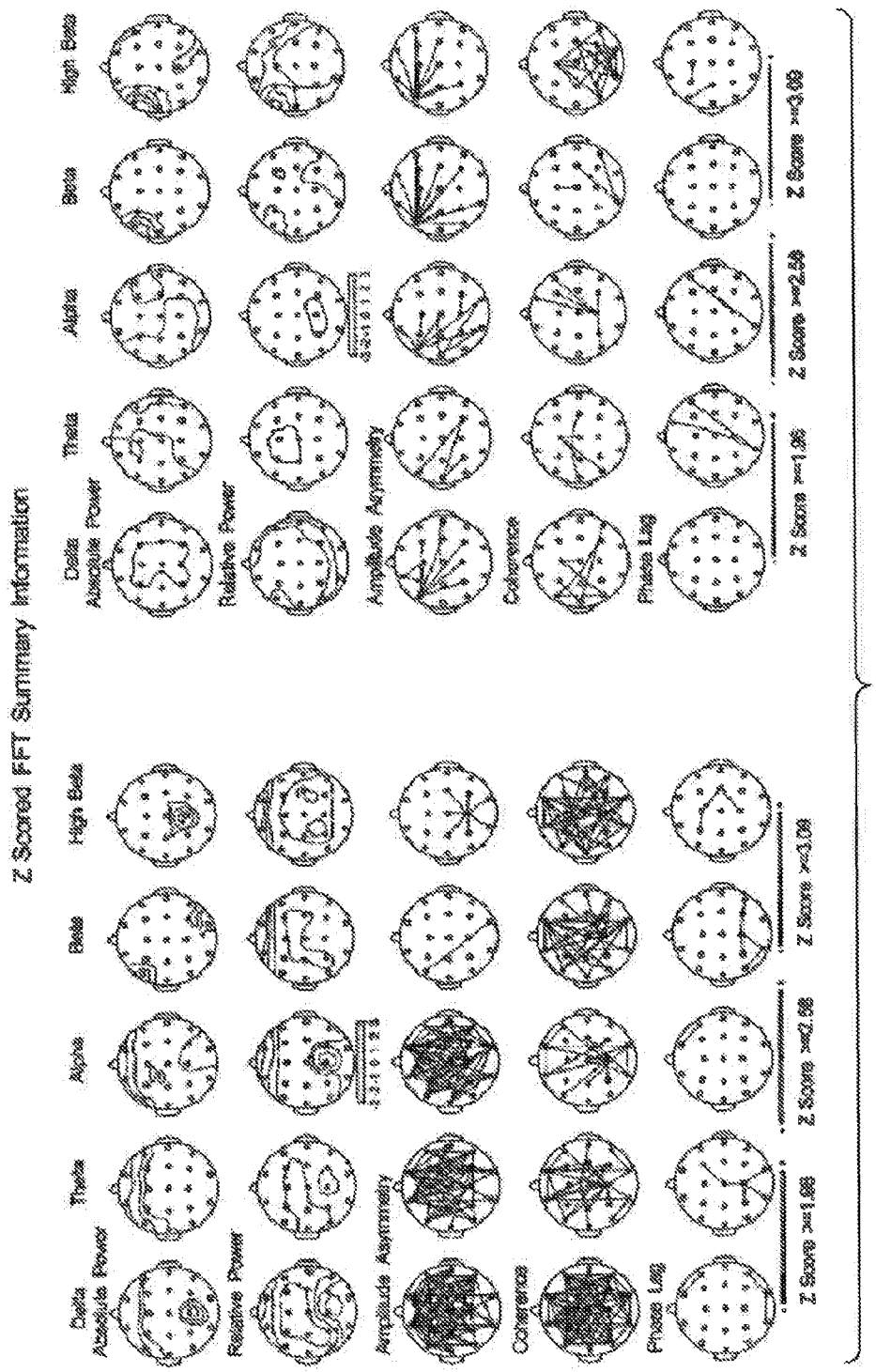
FIG. 8 illustrates pre- and post-treatment QEEGs.

As an example of the ability to multivariate Z-Scores to resolve complex situations, FIG. 8 shows pre- and post-treatment QEEG's taken from a case that required only 23 sessions to produce the changes illustrated. Specifically, the NeuroGuide QEEG maps in FIG. 8 show the effects of 23 sessions of 4-channel Multivariate Proportional live Z-Score training with eyes-open.

The trainee in FIG. 8 was a 12 year-old boy with problems related to impulsivity, behavior, discipline, and hyperactivity. In amplitudes, he had abnormally high slow frontal activity, abnormally low fast frontal activity, and occipital abnormalities in delta and alpha. These also manifested as many significantly abnormal asymmetries. In addition, there was hypercoherence in essentially all frequency bands, and particularly at the very low and very high frequencies.

By using an MVP protocol, clinicians were able to remediate essentially all of these abnormalities in 23 sessions, as shown on the QEEG. Interestingly, one small emerging abnormality appears in the form of left frontal beta and high beta. If anything, this slightly excess activation of the left frontal lobe represents a potential benefit of the system and method, which would be a brightening effect on the trainee's mood. These results are taken from the eyes-open condition, which was the training condition. A different set of changes, also related to normalization of the EEG, was observed in the eyes-closed condition, indicating that the brain was learning self-regulation for both conditions, despite being only trained with eyes-open.

Figures 9A, 9B:
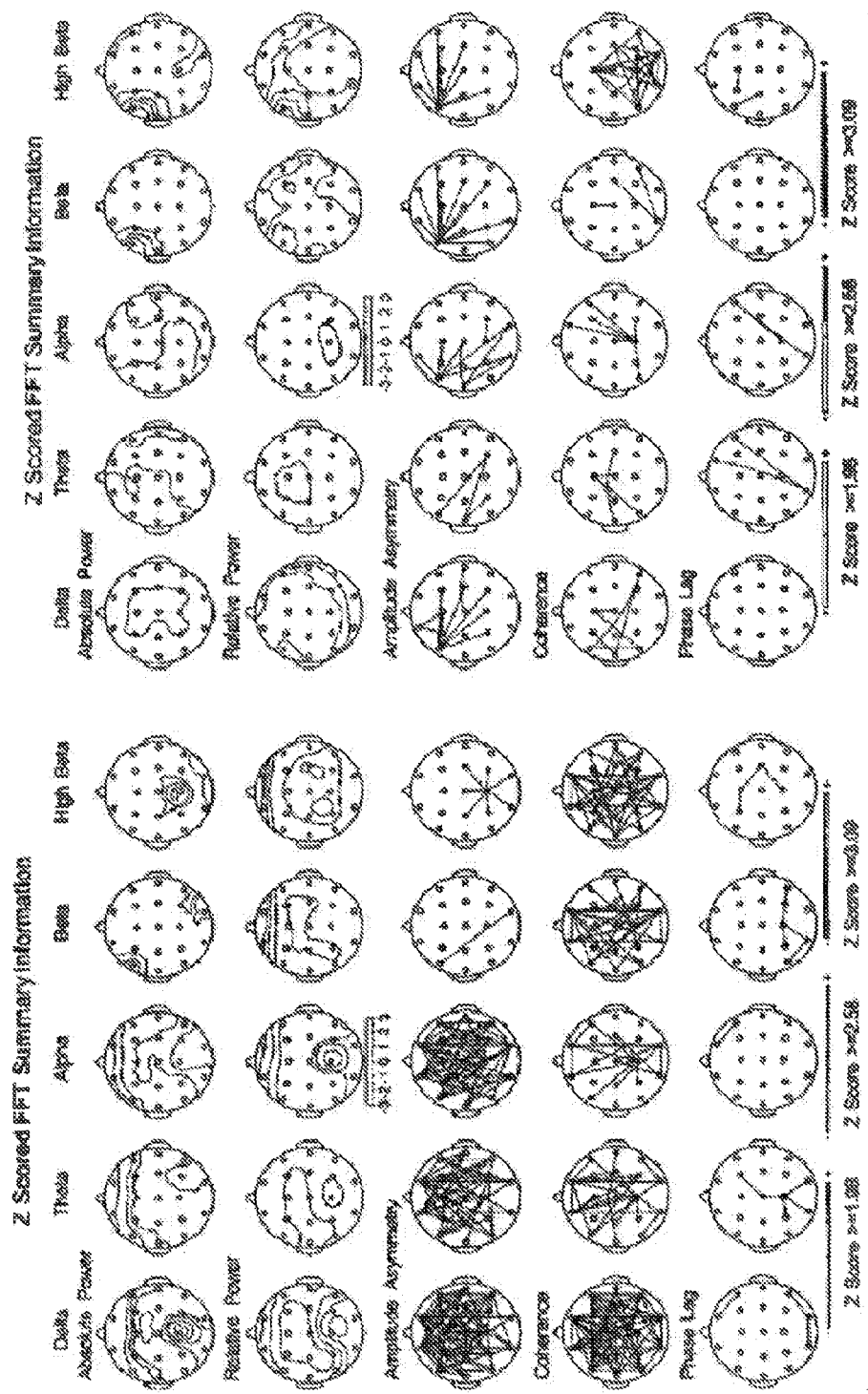
FIGS. 9a & 9b illustrate pre- and post-treatment QEEGs.

The QEEG pre- and post-analyses shown in FIGS. 9a and 9b illustrate the effects of a comprehensive Z-score based EEG neurofeedback training on an individual diagnosed with AD/HD, behavior problems, and aggressive tendencies. The origin of the disorder can be seen in EEG characteristics including excessive frontal slowing, a de-activated posterior cingulate gyrus, and widespread connectivity abnormalities. The subject was treated with 21 sessions of training using sound and video feedback, which was controlled by a computed metric that incorporated 248 different EEG variables in real-time, and provided moment-to-moment proportional feedback which increased as the EEG normalized.

Figure 10A:
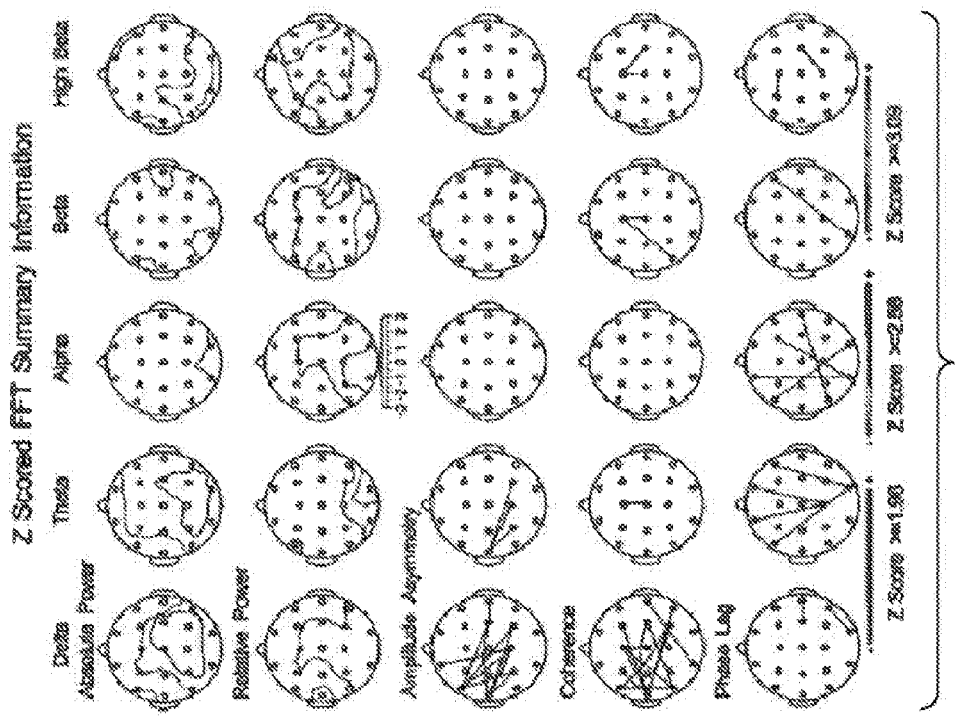
FIGS. 10a & 10b illustrate pre- and post-treatment QEEGs in the eyes closed condition.
Figure 10B:
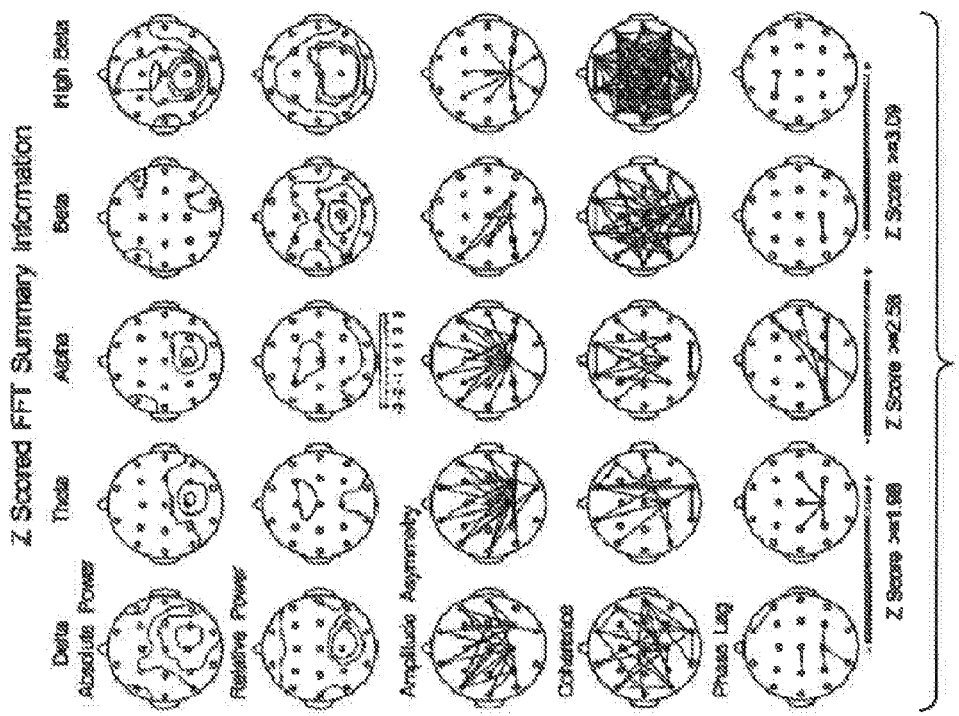

The QEEG's in FIGS. 10a and 10b are taken from the same subject, but are taken in the eyes-closed condition. Note that the training was done eyes-open. This shows that the BEG feedback training is capable of addressing problems that are differently expressed, yet reveal normalization nonetheless. In other words, the training in the eyes-closed condition also produces significant changes evident in the eyes open QEEG. Training at specific sites also typically generalizes to normalize QEEG values at other sites.

The examples in FIGS. 9a, 9b, 10a, and 10b illustrate the role of a variety of brain regulatory dysfunctions on the EEG and on the behavior of the patient. Moreover, when the EEG abnormalities are addressed using a comprehensive feedback program that facilitates self-regulation, the brain is capable of achieving appropriate levels of activation, relaxation, and connectivity as revealed by the EEG.

Figure 11:
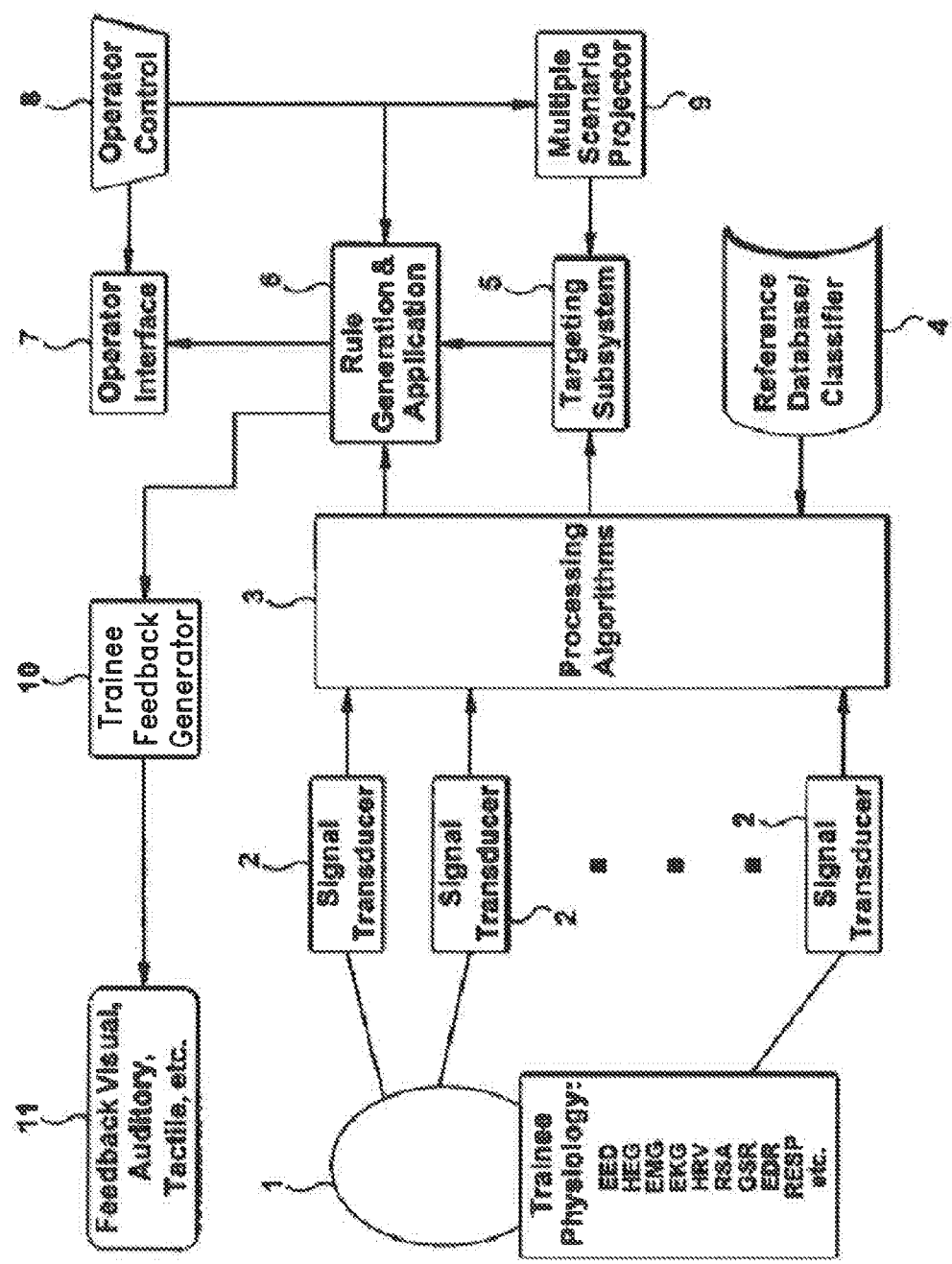
FIG. 11 is a block diagram of the real-time multivariate targeting method for biofeedback.

With reference to FIG. 11, there are illustrated the basic components necessary for an integrated biofeedback system. The Training Subject 1 is connected to one or more instances of appropriate physiological monitoring apparatus 2. The digitized physiological information is processed by mathematical algorithms 3 which will include but not be limited to variability analysis, or other measures.

In this invention, one or more reference criteria are embodied in the Reference Database/Classifier 4. This may be a statistical procedure that yields scores such as z scores in conjunction with a reference or nonnative database, or it may be embodied in a rule-set, algorithm, or classification system. The essential role of this element is to convert physiologically derived variables into quantities that embody information describing possible target states for training.

The information derived from the Processing Algorithms 3 in conjunction with the Reference Database Classifier 4 provide information used by the Targeting Subsystem 5 to determine how well targeted variables conform to established criteria. For example, a z score derived from a normative database might be compared with a defined limit or range, to determine how well the score fits into the category "normal."

The Rule Generation and Application process 6 uses the information from the Processing Algorithms 3 and the Targeting Subsystem 5, to generate and apply rules used to control the feedback process. In a simple embodiment, this procedure would determine whether or not a single score meets its criterion threshold, and proceed to enable visual, auditory, or other feedback.

The Multiple Scenario Projector is used to provide multiple conditions to the Targeting Subsystem 5, so that the Targeting Subsystem produces target results for more than one scenario. Results of this analysis may be expressed and used as a simple quantity, for example, a percentage, figure of merit, or other metric.

The Operator Interface 7 provides summary and control information useful to the Operator. It may include parameter values, statistical information such as z scores, as well as reporting information such as the amount of feedback being provided, which values are currently controlling the feedback, and other measures.

The Trainee Feedback Generator 10 is used to create feedback using the Feedback means or Subsequent Feedback Generator 11 which may be a cathode-ray tube, LCD display, or other type of visual or auditory output. Feedback is used for operant conditioning, concurrent learning and other learning processes. The display may consist of numeric, graphical, or animated material, and may be accompanied by a combination of auditory, vibrotactile, or other feedback.

Through the use of this invention, it becomes possible to guide the self-regulation of the trainee in terms of a complex set of variables, thus defining a desired state, rather than simple manipulation of physiological variables. Whereas existing methods direct the trainee to perform tasks related to a single dimension such as concentration, relaxation, or other characteristics, this invention provides the ability to define complex states which may be characterized by comprehensive qualities including normality, efficiency and performance ability.

In summary, normative EEG biofeedback provides the brain with an opportunity to explore alternative systems of activation and connectivity. The disclosed use of Z-Scores in itself is an important addition to neurofeedback, but it does not provide an "automatic" solution in and of itself. It is not necessarily applicable to every trainee, and the idea of training everyone "to the norm" is not universally applicable.

We do not subscribe to a philosophy of pushing the brain toward the norm as the primary mechanism of change. Rather, the brain will spontaneously seek states of minimum energy and maximum stability, subject to the environment and the experiences it provides. EEG biofeedback provides an alternative environment that include neuro-navigational aids coupled with a means for learning via operant conditioning. Based upon the experience of this navigational information and its own priorities, the brain is then able to discover and retain new ways of functioning.

In general, simply using a Z-Score as a target is not sufficient to produce normalization. In many situations, it will be important to have a whole-head QEEG type of analysis for planning and interpretation of the LZT training. It is necessary to understand and interpret the brain dynamics of the trainee, determine which types of normalization are appropriate, and design and use protocols that are suited to the case at hand. It is also important to wisely use multiple channels and multiple targets, in order to give the brain the information it needs to achieve comprehensive improvements in self-regulation.

The invention has been described in detail with respect to the preferred embodiments, and variations and modifications may occur to those skilled in the art to which the invention pertains.

What is claimed as the invention is:

1. An integrated biofeedback system for normalization and optimization training of a trainee using whole-brain electroencephalographic neurofeedback, said integrated biofeedback system comprising:

an apparatus for simultaneously monitoring from a full range of variable Z-scores from at least four separate sites of the scalp of the trainee, said apparatus comprising an electroencephalograph and at least four signal transducers operatively connected to said electroencephalograph, each transducer of said at least four transducers having a sensor operatively connected to each of said respective signal transducers, said respective sensors being operatively occupied on a separate one of four separate, sites on the trainee's scalp to monitor and transmit time-variable, microvolt surface neuronal potentials along a set of at least four channels for at least four respective separate sites to said at least four respective transducers, said respective at least four transducers generating live digitized physiological information signals corresponding to the respective neuronal potentials transmitted by said respective sensors;

a reference database/classifier module for converting physiologically derived variables into Z-scores embodying a range of training target stages, said reference database/classifier module employing reference criteria by means of statistical procedures that provide means and standard deviations derived from reference data, wherein said reference criteria are embodied in said reference database/classifier module by means of statistical procedures that yield Z-scores in conjunction with a reference database;

a processor operatively connected to both said electroencephalograph and to said reference database/classifier module for using multivariate proportional algorithms and said Z-scores embodying training target states, and generating simultaneous real-time continuous live Z-scores corresponding to said digitized, live physiological information signals, wherein said processor uses multivariate proportional algorithms to compute in real-time, continuous output values in the form of multivariate proportional variables representing a percentage measure of proportionality of the live Z-scores which are within a pre-determined range;

a targeting subsystem operatively connected to said processor for receiving the simultaneous real-time continuous live Z-scores from said processor;

a rule generator and applicator component operationally connected to said processor and to said targeting subsystem for receiving simultaneous real-time continuous live Z-scores from said processor, and for cooperating with said targeting subsystem to control a feedback process to the trainee;
an operator interface including a composite display, wherein a first set of markings on said composite display shows said multivariate proportional variables, a second set of markings on said composite display shows a feedback percentage threshold, and a third set of markings on said composite display shows the cumulative percent time above said threshold, wherein said composite display shows size of the target in standard deviation, and wherein said composite display indicates the times when the multivariate proportional parameter is above a threshold; and
a multiple scenario projector for providing multiple conditions to said targeting subsystem, said targeting subsystem providing target results for more than one scenario;
said targeting subsystem determining from said simultaneous real-time continuous live Z-scores from said processor and from said Z-scores defining particular target results of Z-scores from said multiple scenario projector, how well targeting variables conform to established criteria according to the reference database/classifier module;
a rule generator and application module to determine whether individual real-time live Z-scores received from said targeting subsystem meet a criterion threshold and generating rule generator and application module signals indicating whether said real-time live Z-scores meet the criterion threshold;
a trainee feedback generator operatively connected to said rule generator and application module for generating instantaneous, real-time neurological feedback signals in response to said rule generator and application module signals, said instantaneous, real-time neurological feedback signals being presented to the trainee in a form understandable by the trainee; and
a feedback module operatively connected to said trainee feedback generator for generating instantaneous feedback signals understandable by the trainee in response to receiving instantaneous, real-time neurological feedback signals from said trainee feedback generator for providing real-time feedback to the trainee;
wherein said feedback module includes a display device.

2. An integrated biofeedback system according to claim 1 wherein said real-time feedback to the trainee comprises at least one of operant conditioning of the trainee and concurrent learning of the trainee.

3. An integrated biofeedback system according to claim 1 wherein said instantaneous, real-time neurological feedback signals from said trainee feedback generator is provided for a training function according to a specific metric.

4. An integrated biofeedback system according to claim 3 wherein said specific metric is selected from the group consisting of absolute power, relative power, power ratios for each of said channels, and coherence, phase and asymmetry for each pair of said channels.

5. An integrated biofeedback system according to claim 1 wherein said at least four sites consists of four separate sites, and said sensors at said respective four separate sites transmit microvolt surface neuronal potentials along four channels to provide 248 Z-scores.

6. An integrated biofeedback system according to claim 1 wherein said system transforms all available Z-scores obtained from the trainee into a single metric.

7. An integrated biofeedback system according to claim 6 wherein said single metric comprises a specific metric.

8. An integrated biofeedback system according to claim 7 wherein said specific metric is selected from the group consisting of absolute power, relative power, power ratios for each of said channels, and coherence, phase and asymmetry for each pair of said channels.

9. An integrated biofeedback system according to claim 2 wherein said instantaneous, real-time neurological signals are selected from the group consisting of animations, DVDs, games, sounds and music.

10. An integrated biofeedback system according to claim 1 wherein said real-time feedback to the trainee indicates an aggregate award to be given to the trainee.

11. An integrated biofeedback system according to claim 3 wherein said specific metric is reflective of a comprehensive analysis of all of the Z-scores of the trainee, said specific metric being a training variable, the training variable being adjustable for controlling said subsequent feedback generator for controlling the target size determined by said targeting subsystem.

12. An integrated biofeedback system according to claim 1 wherein said at least four separate sites consists of four sites, and said sensors at said respective separate four sites transmit microvolt surface neuronal potentials along four channels to provide 248 Z-scores.

13. An integrated biofeedback system for normalization and optimization training of a trainee using whole-brain electroencephalographic neurofeedback, said integrated biofeedback system comprising:
an apparatus for simultaneously monitoring from a full range of variable Z-scores from at least two separate sites of the scalp of the trainee, said apparatus comprising an electroencephalograph and at least two signal transducers operatively connected to said electroencephalograph, each transducer of said at least two transducers having a sensor operatively connected to each of said respective signal transducers, said respective sensors being operatively occupied on a separate one of at least two separate sites on the trainee's scalp to monitor and transmit time-variable, microvolt surface neuronal potentials along a set of at least two channels for at least two respective separate sites to said at least two respective transducers, said respective at least two transducers generating live digitized physiological information signals corresponding to the respective neuronal potentials transmitted by said respective sensors;
a reference database/classifier module for converting physiologically derived variables into Z-scores embodying a range of training target stages, said reference database/classifier module employing reference criteria by means of statistical procedures that provide means and standard deviations derived from reference data, wherein said reference criteria are embodied in said reference database/classifier module by means of statistical procedures that yield Z-scores in conjunction with a reference database;
a processor operatively connected to both said electroencephalograph and to said reference database/classifier module for using multivariate proportional algorithms and said Z-scores embodying training target states, and generating simultaneous real-time continuous live Z-scores corresponding to said digitized, live physiological information signals, wherein said processor uses multivariate proportional algorithms to compute in real-time, continuous output values in the form of multivariate proportional variables representing a percentage measure of proportionality of the live Z-scores which are within a pre-determined range;

a targeting subsystem operatively connected to said processor for receiving the simultaneous real-time continuous live Z-scores from said processor;

a rule generator and applicator component operationally connected to said processor and to said targeting subsystem for receiving simultaneous real-time continuous live Z-scores from said processor, and for cooperating with said targeting subsystem to control a feedback process to the trainee;

an operator interface including a composite display, wherein a first set of markings on said composite display shows said multivariate proportional variables, a second set of markings on said composite display shows a feedback percentage threshold, and a third set of markings on said composite display shows the cumulative percent time above said threshold, wherein said composite display shows size of the target in standard deviation, and wherein said composite display indicates the times when the multivariate proportional parameter is above a threshold; and a multiple scenario projector for providing multiple conditions to said targeting subsystem, said targeting subsystem providing target results for more than one scenario;

said targeting subsystem determining from said simultaneous real-time continuous live Z-scores from said processor and from said Z-scores defining particular target results of Z-scores from said multiple scenario projector, how well targeting variables conform to established criteria according to the reference database/classifier module;

a rule generator and application module to determine whether individual real-time live Z-scores received from said targeting subsystem meet a criterion threshold and generating rule generator and application module signals indicating whether said real-time live Z-scores meet the criterion threshold;

a trainee feedback generator operatively connected to said rule generator and application module for generating instantaneous, real-time neurological feedback signals in response to said rule generator and application module signals, said instantaneous, real-time neurological feedback signals being presented to the trainee in a form understandable by the trainee; and a feedback module operatively connected to said trainee feedback generator for generating instantaneous feedback signals understandable by the trainee in response to receiving instantaneous, real-time neurological feedback signals from said trainee feedback generator for providing real-time feedback to the trainee;

wherein said feedback module includes a display device.

14. An integrated biofeedback system for normalization and optimization training of a trainee using whole-brain electroencephalographic neurofeedback, said integrated biofeedback system comprising:

an apparatus for simultaneously monitoring from a full range of variable Z-scores from at least one separate site of the scalp of the trainee, said apparatus comprising an electroencephalograph and at least one signal transducer operatively connected to said electroencephalograph, each transducer of said at least one transducer having a sensor operatively connected to each of said respective signal transducers, said respective sensors being operatively occupied on a separate one of at least one separate site on the trainee's scalp to monitor and transmit time-variable, microvolt surface neuronal potentials along a set of at least one channel for at least one respective separate to said at least one respective transducer, said respective at least one transducers generating live digitized physiological information signals corresponding to the respective neuronal potentials transmitted by said respective sensors;

a reference database/classifier module for converting physiologically derived variables into Z-scores embodying a range of training target stages, said reference database/classifier module employing reference criteria by means of statistical procedures that provide means and standard deviations derived from reference data, wherein said reference criteria are embodied in said reference database/classifier module by means of statistical procedures that yield Z-scores in conjunction with a reference database;

a processor operatively connected to both said electroencephalograph and to said reference database/classifier module for using multivariate proportional algorithms and said Z-scores embodying training target states, and generating simultaneous real-time continuous live Z-scores corresponding to said digitized, live physiological information signals, wherein said processor uses multivariate proportional algorithms to compute in real-time, continuous output values in the form of multivariate proportional variables representing a percentage measure of proportionality of the live Z-scores which are within a pre-determined range;

a targeting subsystem operatively connected to said processor for receiving the simultaneous real-time continuous live Z-scores from said processor;

a rule generator and applicator component operationally connected to said processor and to said targeting subsystem for receiving simultaneous real-time continuous live Z-scores from said processor, and for cooperating with said targeting subsystem to control a feedback process to the trainee;

an operator interface including a composite display, wherein a first set of markings on said composite display shows said multivariate proportional variables, a second set of markings on said composite display shows a feedback percentage threshold, and a third set of markings on said composite display shows the cumulative percent time above said threshold, wherein said composite display shows size of the target in standard deviation, and wherein said composite display indicates the times when the multivariate proportional parameter is above a threshold; and a multiple scenario projector for providing multiple conditions to said targeting subsystem, said targeting subsystem providing target results for more than one scenario;

said targeting subsystem determining from said simultaneous real-time continuous live Z-scores from said processor and from said Z-scores defining particular target results of Z-scores from said multiple scenario projector, how well targeting variables conform to established criteria according to the reference database/classifier module;

a rule generator and application module to determine whether individual real-time live Z-scores received from said targeting subsystem meet a criterion threshold and generating rule generator and module signals indicating whether said real-time live Z-scores meet the criterion threshold;

a trainee feedback generator operatively connected to said rule generator and application module for generating instantaneous, real-time neurological feedback signals in response to said rule generator and application module signals, said instantaneous, real-time neurological feedback signals being presented to the trainee in a form understandable by the trainee; and a feedback module operatively connected to said trainee feedback generator for generating instantaneous feedback signals understandable by the trainee in response to receiving instantaneous, real-time neurological feedback signals from said trainee feedback generator for providing real-time feedback to the trainee;

wherein said feedback module includes a display device.

* * * * *